(12) United States Patent
Ishikura et al.

(10) Patent No.: US 7,229,985 B2
(45) Date of Patent: Jun. 12, 2007

(54) AMORPHOUS SUBSTANCE OF TRICYCLIC TRIAZOLOBENZAZEPINE DERIVATIVE

(75) Inventors: Toyoaki Ishikura, Kanagawa-Ken (JP); Takayuki Ishizawa, Kangawa-Ken (JP); Kenji Suemune, Kanagawa-Ken (JP); Mayumi Ishiwata, Kanagawa-Ken (JP); Chikako Udagawa, Kanagawa-Ken (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 75 days.

(21) Appl. No.: 10/500,071

(22) PCT Filed: Dec. 25, 2002

(86) PCT No.: PCT/JP02/13558

§ 371 (c)(1),
(2), (4) Date: Jun. 25, 2004

(87) PCT Pub. No.: WO03/055886

PCT Pub. Date: Jul. 10, 2003

(65) Prior Publication Data

US 2005/0130955 A1 Jun. 16, 2005

(30) Foreign Application Priority Data

Dec. 26, 2001 (JP) ............................. 2001-393016

(51) Int. Cl.
*C07D 487/04* (2006.01)
*A61K 31/55* (2006.01)
*A61K 9/14* (2006.01)
*A61K 47/38* (2006.01)

(52) U.S. Cl. .................................. 514/212.06; 540/521

(58) Field of Classification Search ................ 540/521; 514/212.06

See application file for complete search history.

(56) References Cited

U.S. PATENT DOCUMENTS 6,372,735 B1 * 4/2002 Ohtsuka et al. ......... 514/212.06

FOREIGN PATENT DOCUMENTS

WO 99/16770 A1 4/1999

OTHER PUBLICATIONS

Hancock et al. (Pharmaceutical Research, vol. 17, No. 4, 2000).*

* cited by examiner

*Primary Examiner*—Bruck Kifle
(74) *Attorney, Agent, or Firm*—Heller Ehrman LLP

(57) ABSTRACT

Disclosed are 2-(1-isopropoxycarbonyloxy-2-methylpropyl)-7,8-dimethoxy-4(5$\underline{H}$), 10-dioxo-2$\underline{H}$-1,2,3-triazolo[4,5-c][1]benzazepine, which has been rendered amorphous and possesses improved absorption and dissoluvability, and a pharmaceutical composition comprising the same. Also disclosed are processes for producing 2-(1-isopropoxycarbonyloxy-2-methylpropyl)-7,8-dimethoxy-4(5$\underline{H}$), 10-dioxo-2$\underline{H}$-1,2,3-triazolo[4,5-c][1]benzazepine, which has been rendered amorphous, and a pharmaceutical composition comprising the same.

13 Claims, 3 Drawing Sheets

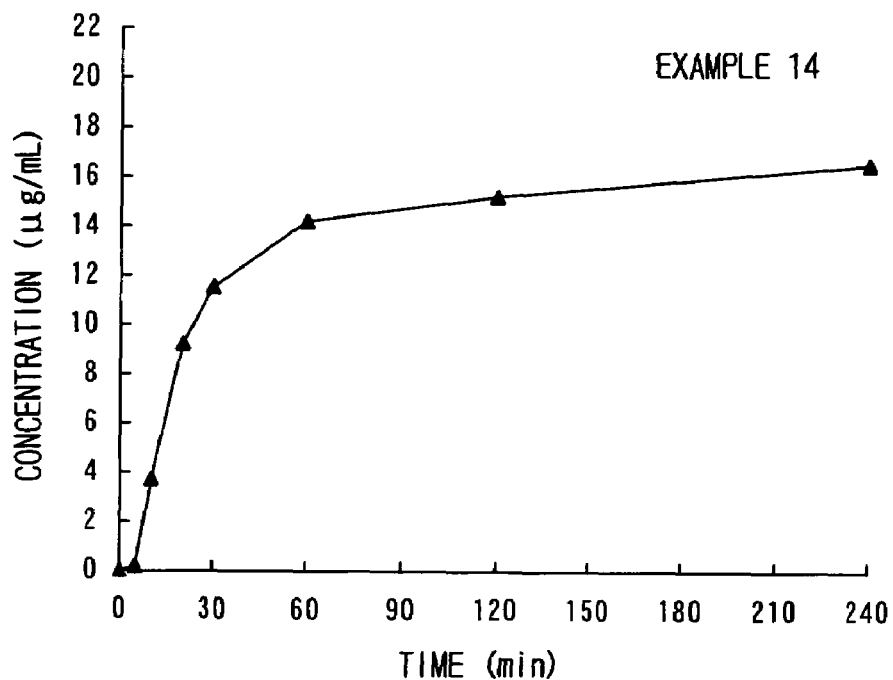
F I G. 4
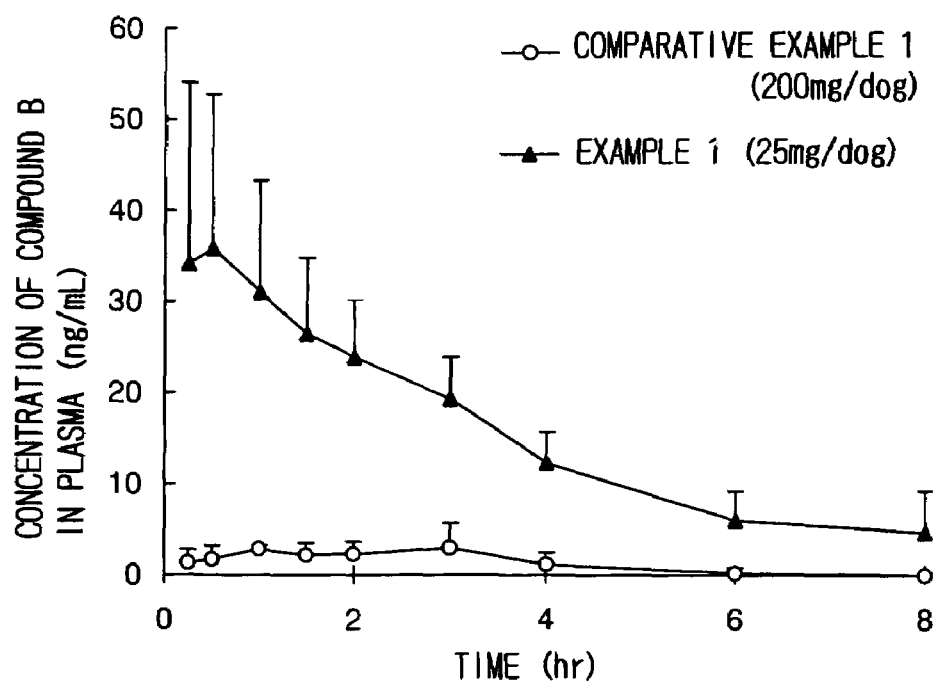
F I G. 5

AMORPHOUS SUBSTANCE OF TRICYCLIC TRIAZOLOBENZAZEPINE DERIVATIVE

BACKGROUND OF THE INVENTION

1. Field of the Invention

The present invention relates to 2-(1-isopropoxycarbonyloxy-2-methylpropyl)-7,8-dimethoxy-4(5H), 10-dioxo-2H-1,2,3-triazolo[4,5-c][1]benzazepine, which is in amorphous form and possesses improved dissolution and absorption, and a pharmaceutical composition comprising the same.

2. Background Art 2-(1-Isopropoxycarbonyloxy-2-methylpropyl)-7,8-dimethoxy-4(5H), 10-dioxo-2H-1,2,3-triazolo[4,5-c][1]benzazepine (hereinafter referred to as "compound A") is a compound, represented by the following chemical structural formula, as disclosed in WO 99/16770 (Japanese Patent No. 3188482 and U.S. Pat. No. 6,372,735) (the disclosure of each of these publications is incorporated herein by reference).

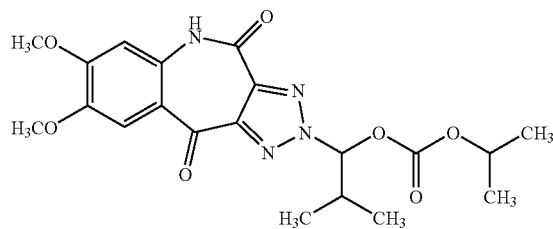

Upon oral administration, this compound exhibits a mast cell membrane stabilizing action and an inhibitory activity against allergic inflammation and thus is expected to be used clinically as oral antiallergic agents. Since, however, compound A, when used in a crystalline form (hereinafter referred to as "crystalline compound A"), is poorly soluble, the compound contained in a formulation is hardly absorbed within the digestive tract and is less likely to be absorbed in a body. Therefore, improving solubility and bioavailability of crystalline compound A is required for the design and production of oral preparations.

The present inventors have attempted various methods with a view to improving the dissolvability of crystalline compound A. As a result, it was found that the dissolution of crystalline compound A with the aid of an acidic or basic additive is difficult due to the absence of a functional group, which is dissociated or protonated in a pharmaceutically acceptable pH range, in the structure of compound A. Further, even after inclusion compounds, such as cyclodextrins, or various surfactants, polymeric compounds or the like are added, crystalline compound A could not be substantially solubilized without difficulties. Furthermore, the solubility of crystalline compound A in glycerin, propylene glycol, Macrogol 400 and the like was not on such a level that can make crystalline compound A pharmaceutically usable. In addition, an experiment in which a pulverized crystal of crystalline compound A is prepared according to the description of Japanese Patent Laid-Open No. 185013/1987 disclosing a drug, which has been rendered easily absorbable by pulverizing was carried out. The treated drug is orally administered to experimental animals such as dogs. As a result, it was found that an improvement in absorption of preparations using crystalline compound A is not more than expected.

A technique known for improving the dissolution of the hardly soluble crystalline compound is to convert the crystalline compound to an amorphous compound (for example, Yu L., Advanced Drug Delivery Reviews, Vol. 48, p. 29, 2001). Specific examples thereof include heat melting, rapid crystallization by the addition of a hardly soluble solvent, lyophilization, spray drying, preparation of solid dispersion, mechanochemical conversion (such as commutation), and dehydration from crystalline hydrate. Most of common techniques for rendering drugs amorphous, however, could not be applied to crystalline compound A due to the occurrence of unfavorable phenomena including that crystalline compound A is decomposed upon heat melting due to closeness of the melting point to the decomposition point; precipitation as a crystal is observed even by the rapid crystallization method; there is no proper solvent for lyophilization; crystalline compound A is not heat melted even in a thermal plastic substance and, even when dissolved in a solvent together with various additives, causes crystallization during the removal of the solvent by distillation under the reduced pressure (that is, a solid dispersion cannot be prepared by the melting method and the solvent distilling-off method); pulverization or extruder treatment does not render crystalline compound A amorphous or results in the formation of a decomposition product; and any hydrate is not formed.

SUMMARY OF THE INVENTION

The present inventors have now found that, when compound A is dissolved in a solvent to prepare a solution which is then spray dried, the spray dried product has significantly lowered degree of crystallization. Since, however, crystalline compound A is hardly soluble in water as well as in various solvents, this method raised an issue about the selection of a proper solvent for spray drying. The present inventors have found that crystalline compound A can be rendered amorphous by dissolving compound A in a certain solvent and then spray drying the solution. They have further found that the incorporation of methylcellulose and/or hydroxypropylmethylcellulose can suppress the crystallization of the amorphized compound A. The present invention has been made based on such finding.

Accordingly, an object of the present invention is to provide compound A which has been rendered amorphous and possesses improved solubility and bioavailability, a composition comprising the same, and production processes of compound A and the composition.

According to the present invention, there is provided amorphous compound A which does not have any diffraction peak in a powder X-ray diffraction pattern and has a solubility of 15 to 20 μg/mL in a 1 wt % methylcellulose solution at 37° C.

According to the present invention, there is also provided a composition which can suppress the crystallization of amorphous compound A. The composition comprises the amorphous compound A according to the present invention and methylcellulose and/or hydroxypropylmethylcellulose.

Furthermore, according to the present invention, there is provided a process for producing amorphous compound A. The process comprises the steps of: dissolving 2-(1-isopropoxycarbonyloxy-2-methylpropyl)-7,8-dimethoxy-4(5H), 10-dioxo-2H-1,2,3-triazolo[4,5-c][1]benzazepine in methylene chloride to prepare a solution; and then spray-drying the solution.

BRIEF DESCRIPTION OF THE DRAWINGS

FIG. 4 is a diagram showing the solubility in water of a capsule preparation comprising amorphous compound A produced in Example 14; and FIG. 5 is a diagram showing a change in level of drug in plasma in an experiment in which each of amorphous compound A produced in Example 1 and crystalline compound A produced in Comparative Example 1 is suspended in a 1 wt % aqueous methylcellulose solution to prepare suspensions which are then orally administered to beagles.

DETAILED DESCRIPTION OF INVENTION

Figure 1:
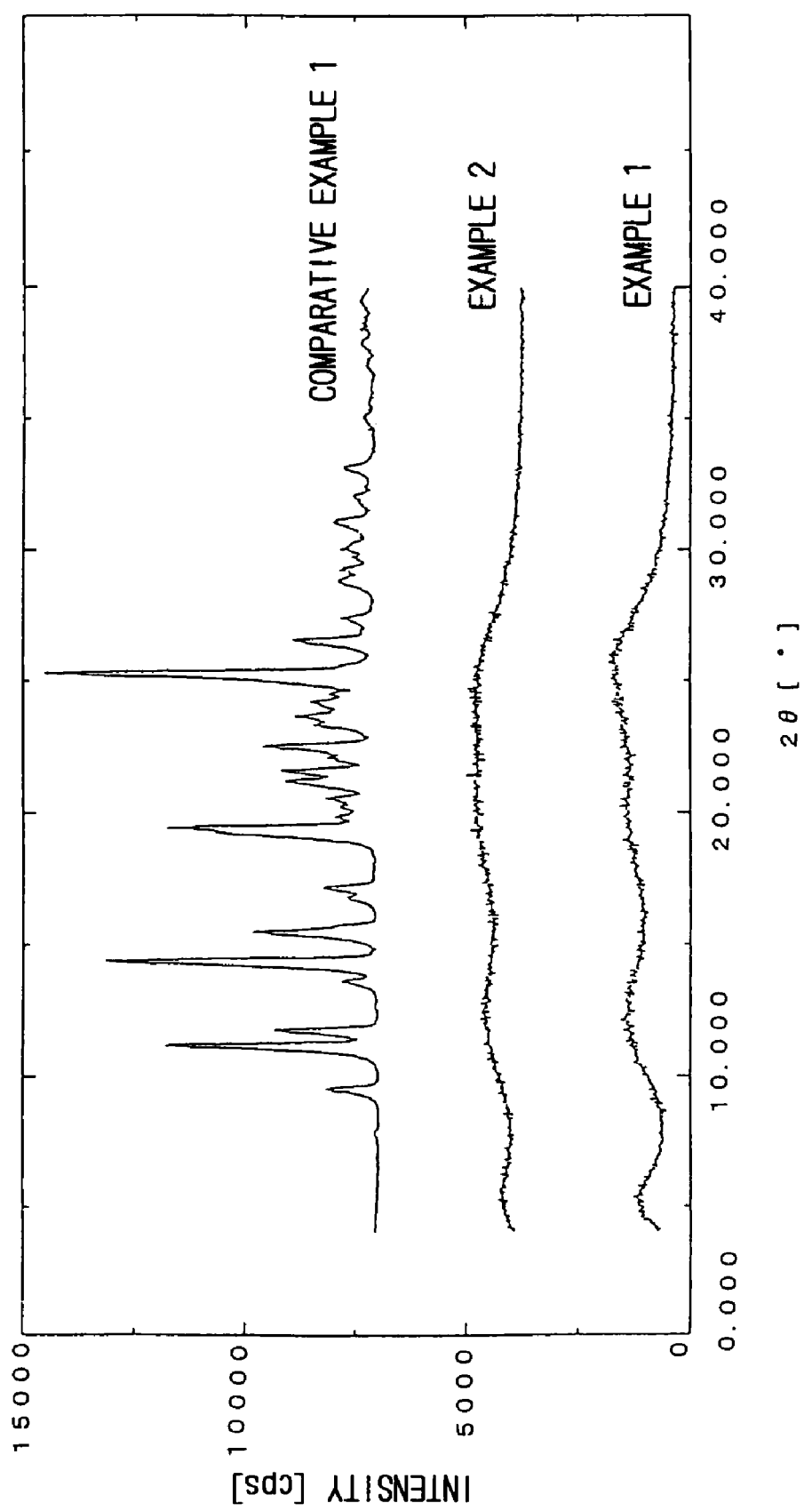
FIG. 1 is powder X-ray diffraction patterns of amorphous compound A and an amorphous composition produced in Example 1 and Example 2, respectively, and crystalline compound A produced in Comparative Example 1.

Amorphous Compound A and Production Process Thereof

Amorphous compound A according to the present invention refers to a compound in a solid state which does not have any characteristic diffraction peak in a powder X-ray diffraction pattern. Further, amorphous compound A according to the present invention has a solubility of 15 to 20 µg/mL in a 1 wt % methylcellulose solution at 37° C.

Amorphous compound A according to the present invention can be produced by dissolving compound A in methylene chloride and then spray drying the solution.

Crystalline compound A is hardly soluble in water as well as in various general-purpose solvents, and the solubility of crystalline compound A in methylene chloride is as low as about 1% by weight. However, once crystalline compound A is dissolved in methylene chloride, compound A is not precipitated as a crystal even when the solution is concentrated to a compound A concentration exceeding 15% by weight. Further, regardless of whether or not the concentration procedure is carried out, amorphous compound A can be provided by spray drying the solution of compound A in methylene chloride. Setting the concentration of the solution used for spray drying at a high value is preferred for spray dried product recovery efficiency enhancement purposes or spray drying treatment time shortening purposes. Accordingly, in a preferred embodiment of the present invention, after the concentration procedure, the solution of compound A in methylene chloride is spray dried. The concentration of compound A in the methylene chloride solution to be spray dried is preferably in the range of 1 to 15% by weight, more preferably in the range of 3 to 10% by weight. Details of spray drying and specific methods for spray drying will be described later.

Amorphous compound A according to the present invention exhibits improved solubility particularly in water over crystalline compound A and thus is preferably used as a pharmaceutical bulk, especially as a pharmaceutical bulk for the production of a pharmaceutical composition for oral administration. Compound A can be used for prophylaxis or therapy of allergic diseases. Allergic diseases include, for example, bronchial asthma, eczema, hives, allergic gastrointestinal injury, allergic rhinitis, and allergic conjunctivitis.

Amorphous compound A according to the present invention as such may be administered orally. In general, however, amorphous compound A according to the present invention, together with a conventional pharmaceutically acceptable carrier, is formulated into oral preparations. Amorphous compound A according to the present invention can be formulated, by using, as carriers, excipients (for example, lactose, crystalline cellulose, starch, and calcium hydrogenphosphate), binders (for example, starch, carmellose sodium, and hydroxypropylcellulose), disintegrants (for example, carmellose calcium, croscarmellose sodium), lubricants (for example, magnesium stearate and talc) and the like, into dosage forms commonly supplied in medical fields, that is, tablets, capsules, granules, dry syrup, and various liquid preparations including syrup prepared by a conventional method. Further, these various preparations may be in a sustained release form which has persistent effect for a long period of time.

According to another aspect of the present invention, there is provided a method for preventing or treating an allergic disease, said method comprising the step of administering amorphous compound A according to the present invention to an animal including a human. Further, according to a further aspect of the present invention, there is provided use of amorphous compound A according to the present invention, for the production of an antiallergic agent.

Composition Comprising Amorphous Compound A

According to the present invention, there is provided a composition, especially a pharmaceutical composition, comprising amorphous compound A. In a preferred embodiment of the present invention, there is provided a pharmaceutical composition particularly for oral administration.

In a preferred embodiment of the present invention, amorphous compound A according to the present invention, together with methylcellulose or hydroxypropylmethylcellulose, is formulated in the composition. Compound A contained in this composition can maintain good solubility in solvents such as water for a long period of time. While there is no intention of being bound by the following theory, it is believed that methylcellulose and hydroxypropylmethylcellulose can suppress the crystallization of amorphatized compound A to maintain good solubility of amorphous compound A for a long period of time. Even when the amount of methylcellulose and hydroxypropylmethylcellulose formulated is small, unexpectedly, the effect of maintaining compound A in an amorphous state is good. In a more preferred embodiment of the present invention, however, when the amount of amorphous compound A is presumed to be 1, the mixing ratio (on a weight basis) to the total amount of methylcellulose and hydroxypropylmethylcellulose is preferably in the range of 0.01 to 2. The lower limit of the mixing ratio is more preferably 0.05, and the upper limit of the mixing ratio is more preferably 1.

In another aspect of the present invention, there is provided composition comprising amorphous compound A according to the present invention and a polymeric compound the formulation of which is generally pharmaceutically acceptable. The polymeric compound may be selected from the group consisting of ethylcellulose, hydroxypropylmethylcellulose phthalate, hydroxypropylcellulose, carboxymethylethylcellulose, polyvinyl pyrrolidone, polyvinyl acetal diethylaminoacetate, methacrylic acid copolymer L, aminoalkyl methacryl acrylate copolymer E, and vinyl acetate-vinylpyrrolidone copolymer. These polymeric compounds may be used as a mixture of two or more.

The composition according to the present invention can be produced by preparing amorphous compound A and then physically mixing amorphous compound A with methylcellulose or hydroxypropylmethylcellulose or a polymeric compound.

In another embodiment of the present invention, the composition according to the present invention can be produced by dissolving both compound A and methylcellulose or hydroxypropylmethylcellulose or a polymeric compound in methylene chloride and then spray drying the solution.

When only methylene chloride is used, some of polymeric compounds are not dissolved or are low in dissolution rate. For example, methylcellulose, hydroxypropylmethylcellulose, hydroxypropylmethylcellulose phthalate, carboxymethylethylcellulose, and methacrylic acid copolymer L have this tendency. When such polymeric compounds are used, the use of a mixed solvent prepared by adding a lower alcohol such as methanol or ethanol to methylene chloride can solve this problem and can realize the dissolution thereof. In a preferred embodiment of the present invention, the lower alcohol is an alkyl alcohol having 1 to 3 carbon atoms.

In a preferred embodiment of the present invention, the composition is produced by dissolving crystalline compound A in methylene chloride to prepare a solution, then optionally concentrating the solution, adding a lower alcohol to the solution or the concentrate to prepare a mixed solution, dissolving the above polymeric compound in the mixed solution to prepare a solution, and spray drying the solution, or by mixing a solution of compound A in methylene chloride with a separately prepared solution or suspension of the above polymeric compound in a lower alcohol, stirring the mixture to prepare a solution, and spray drying the solution.

The mixing ratio between methylene chloride and lower alcohol is not particularly limited so far as the mixture, together with compound A and methylcellulose or hydroxypropylmethylcellulose or a polymeric compound, can form a solution. The weight ratio of the lower alcohol to methylene chloride, however, is preferably such that the amount of the lower alcohol is not more than three times, more preferably not more than 1.5 times, the amount of methylene chloride.

The composition according to the present invention thus obtained as such may be administered orally. In general, however, the composition according to the present invention, together with a conventional pharmaceutically acceptable carrier, is formulated into oral preparations. Carriers usable herein include those as described above in connection with amorphous compound A.

Further, according to another aspect of the present invention, there is provided a method for preventing or treating an allergic disease, said method comprising the step of administering the composition according to the present invention comprising amorphous compound A to an animal including a human. According to a further aspect of the present invention, there is provided use of the pharmaceutical composition according to the present invention comprising amorphous compound A, for the production of an antiallergic agent.

Spray Drying

In the present invention, spray drying may be carried out in the same apparatus as commonly used in fields such as food products, pharmaceutical products, and various chemical industries. When a lower alcohol is added to the solution to be spray dried, however, the use of an explosion-proof type spray dryer is preferred.

When the time required from mist formation to drying in the step of spray drying is long, disadvantageously, there is a significant tendency of the presence of crystalline compound A and amorphous compound A as a mixture. In order to provide the amorphous compound free from the crystalline compound, minimizing the diameter of the spray mist is preferred. To this end, in addition to the following operating conditions of the spray dryer, the specifications and capacity of a solution spray device are also important. The spray device is preferably a two fluid nozzle or a four fluid nozzle rather than a rotary atomizer. Since, however, which device is to be used also depends upon operation conditions, the spray device is not necessarily limited to the two fluid nozzle and four fluid nozzle.

In spray drying, as described above, since the spray mist diameter is reduced, the particle diameter of the spray dried product is also reduced. In addition to cyclone commonly used in the art, various filters may be used for collection of the spray dried product.

Regarding operating conditions for the spray dryer, in supply of gas into a drying chamber, when the solvent is methylene chloride, gases, commonly used in spray drying, including compressed air may be used. When the solvent is a mixed solvent composed of methylene chloride and a lower alcohol, an explosion-preventive oxygen-free gas such as nitrogen gas is used. Supply gas temperature is preferably in the range of 40 to 120° C., more preferably in the range of 50 to 100° C. When mist is formed using a spray nozzle, the supply gas pressure is preferably in the range of 0.05 to 1.5 MPa and more preferably in the range of 0.1 to 0.7 MPa from the viewpoint of reducing the spray mist diameter as described above. The feed speed of the solution containing compound A is not particularly limited, because it may vary depending upon a difference in spray mist formation method, supply gas pressure, and the size of the spray dryer.

EXAMPLES

The present invention is further illustrated by the following Examples that are not intended as a limitation of the invention.

In the following Examples and Comparative Examples, a powder X-ray diffraction apparatus was used for evaluation under the following measuring conditions.

Apparatus: RINT 2200 (manufactured by Rigaku Industrial Corporation)

Measuring conditions: lamp; Cu, tube voltage; 40 kV, tube current; 20 mA, monochromator; graphite, scanning speed; 4°/min, scanning step; 0.02°, scanning axis; 2 θ/θ, divergent slit; 1°, scattering slit; 1°, light receiving slit; 0.30 mm, scanning range; 3 to 40°

Comparative Example 1

A light yellow powder produced according to the method described in Example 20 of WO 99/16770 was dissolved in methylene chloride to prepare a solution which was then recrystallized from methanol to give crystalline compound A. The crystalline compound A exhibited characteristic diffraction peaks as analyzed by powder X-ray diffractometry.

Example 1

The crystalline compound A (30 g) produced in Comparative Example 1 was dissolved in 2000 g of methylene chloride to prepare a solution which was then concentrated under the reduced pressure to give a 5 wt % solution. The concentrated solution was treated in a spray drier (Model GS 31, manufactured by YAMATO SCIENTIFIC CO., LTD.) (air feed temp.: 70° C., liquid feed rate: 10 g of solution per min) to give 23 g of a light yellow amorphous powder. The powder did not exhibit any characteristic diffraction peak as analyzed by powder X-ray diffractometry.

Example 2

The crystalline compound A (360 g) produced in Comparative Example 1 was dissolved in 2600 g of methylene chloride to prepare a solution which was then concentrated under the reduced pressure to give a 8 wt % concentrated solution. The concentrated solution was mixed with a solution of 72 g of methylcellulose (Metlose SM15, manufactured by The Shin-Etsu Chemical Co., Ltd.) in 2700 g of methanol. The mixed solution was treated in a spray drier (Model CL-8, manufactured by Ohkawara Kakohki Co., Ltd.) (air feed temp.: 90° C., liquid feed rate: 20 g of solution per min) to give 290 g of a light yellow powder. The powder did not exhibit any characteristic diffraction peak as analyzed by powder X-ray diffractometry.

Example 3

The crystalline compound A (20 g) produced in Comparative Example 1 was dissolved in 1400 g of methylene chloride to prepare a solution which was then concentrated under the reduced pressure to give a 4 wt % concentrated solution. Methanol (320 g) was added to the concentrated solution, and 4 g of hydroxypropylmethylcellulose (TC-5R, manufactured by The Shin-Etsu Chemical Co., Ltd.) was further added and dissolved therein to prepare a solution. The solution was treated in a spray drier (Model GS 31) (air feed temp.: 90° C., liquid feed rate: 10 g of solution per min) to give 13 g of a light yellow powder. The powder did not exhibit any characteristic diffraction peak as analyzed by powder X-ray diffractometry.

Example 4

The crystalline compound A (8 g) produced in Comparative Example 1 was dissolved in 560 g of methylene chloride to prepare a solution which was then concentrated under the reduced pressure to give a 4 wt % concentrated solution. Methanol (120 g) was added to the concentrated solution, and 1.6 g of methylcellulose (Metlose SM 15) and 1.6 g of hydroxypropylmethylcellulose (TC-5R) were further added and dissolved therein to prepare a solution. The solution was treated in a spray drier (Model GS 31) (air feed temp.: 90° C., liquid feed rate: 10 g of solution per min) to give 7 g of a light yellow powder. The powder did not exhibit any characteristic diffraction peak as analyzed by powder X-ray diffractometry.

Examples 5 to 13

In Examples 5 to 13, compounds were produced in the same manner as described above, except that only the polymer compound was changed.

Specifically, crystalline compound A (8 g) produced in Comparative Example 1 was dissolved in 560 g of methylene chloride to prepare a solution which was then concentrated under the reduced pressure to give a 4 wt % concentrated solution. Methanol (120 g) was added to the concentrated solution, and 1.6 g of the following polymer compound was further added and dissolved therein.

Example 5: Ethylcellulose (Shin-Etsu ethylcellulose, manufactured by The Shin-Etsu Chemical Co., Ltd.)

Example 6: Hydroxypropylmethylcellulose phthalate (HPMCP, manufactured by The Shin-Etsu Chemical Co., Ltd.)

Example 7: Hydroxypropylcellulose (NISSO-HPC-L, manufactured by Nippon Soda Co., Ltd.)

Example 8: Carboxymethylethylcellulose (CMEC, manufactured by Freund Industrial Co., Ltd.)

Example 9: Polyvinyl pyrrolidone (Kollidon K30, manufactured by Basf Japan)

Example 10: Polyvinyl acetal diethylaminoacetate (AEA SANKYO, manufactured by SANKYO CO., LTD.)

Example 11: Methacrylic acid copolymer L (Eudragit L, manufactured by Roehm Pharma)

Example 12: Aminoalkyl methacryl acrylate copolymer E (Eudragit E, manufactured by Roehm Pharma)

Example 13: Vinyl acetate-vinylpyrrolidone copolymer (Plasdone S-630, manufactured by ISP)

The solutions thus obtained were treated in a spray drier (Model GS 31) (air feed temp.: 90° C., liquid feed rate: 10 g of solution per min) to give light yellow powders. All the powders did not exhibit any characteristic diffraction peak as analyzed by powder X-ray diffractometry.

Example 14

Amorphous compound (10.0 g) produced in Example 1, mannitol (10.0 g), hydroxypropylmethylcellulose (2.0 g), sodium carboxymethyl starch (5.0 g), and magnesium stearate (0.135 g) were mixed together, and the mixture was tabletted (tabletting pressure: 2 tons/tablet) by a rotary tablet machine. The tablets were disintegrated with mortar/pestle, followed by particle size regulation with a sieve (No. JP 30). Sodium carboxymethyl starch (10.0 g) was added to and mixed with the granules thus obtained, and 371.35 mg of the mixture was filled into a hydroxypropylmethylcellulose capsule (No. 0) to prepare a capsule preparation containing 100 mg of the amorphous compound produced in Example 1 per preparation.

Test Example 1

Powder X-Ray Diffraction

The powders produced in Examples 1 and 2 and crystalline compound A produced in Comparative Example 1 were tested for crystallinity (degree of crystallization). The results were as shown in FIG. 1.

Crystalline compound A produced in Comparative Example 1 exhibited characteristic diffraction peaks attributable to regular spacial configuration of the molecule constituting a crystal lattice as analyzed by powder X-ray diffractometry. On the other hand, none of the amorphous compound produced in Example 1 and the amorphous composition produced in Example 2 according to the present invention exhibits any characteristic diffraction peak as analyzed by powder X-ray diffractometry. The same results were obtained for the composition produced in Examples 3 to 13. These facts demonstrate that all of the amorphous compound and amorphous compositions of the examples of the present invention are amorphous.

Test Example 2

Dissoluvability Test (1)

Figure 2:
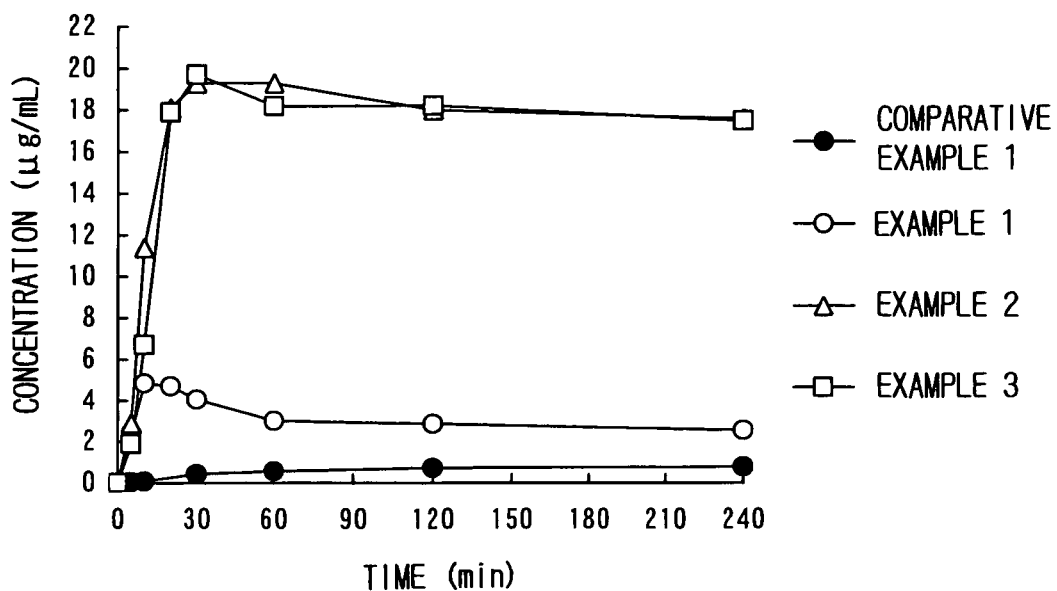
FIG. 2 is a diagram showing the solubility in water of amorphous compound A produced in Example 1, amorphous compositions produced in Examples 2 and 3, and crystalline compound A produced in Comparative Example 1.
Figure 3:
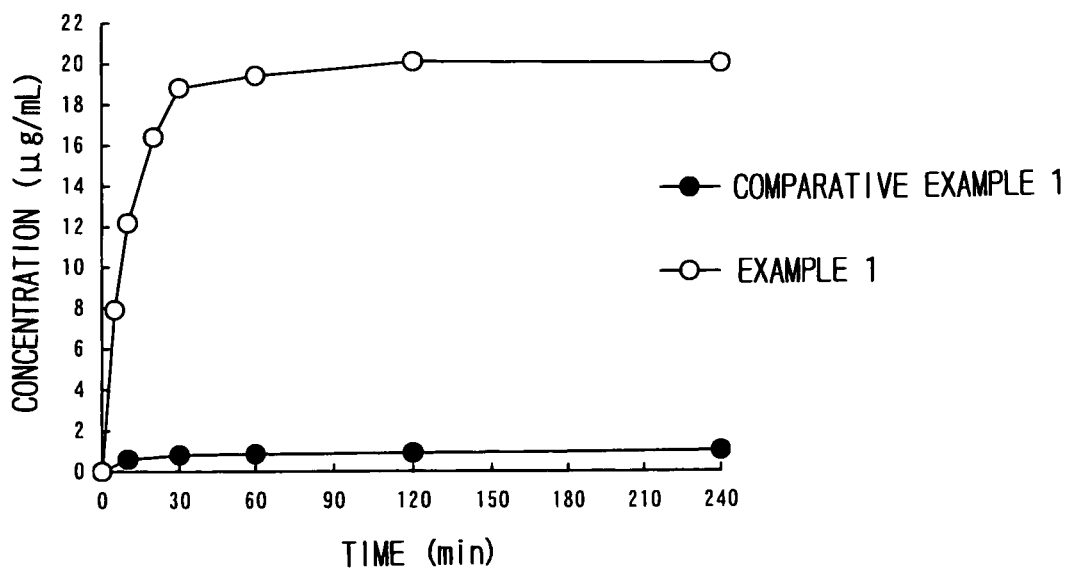
FIG. 3 is a diagram showing the solubility of amorphous compound A in a 1 wt % aqueous methylcellulose solution produced in Example 1 and crystalline compound A produced in Comparative Example 1.

Water or a 1 wt % aqueous methylcellulose solution was provided as a test liquid, and solubility of various samples in the test liquid was examined. Each sample in an amount of about 100 mg in terms of compound A was added to 500 mL of the test liquid kept at 37° C., and the mixture was stirred with a paddle at 200 rpm. Sampling was carried out at predetermined time intervals, and the samples were filtered through a membrane filter (Sumplep LCR 13-LG, manufactured by Millipore Corporation). The concentration of compound A in each of the filtrates was analyzed by HPLC. The results are shown in FIGS. 2 and 3.

In Test Example 2, HPLC was carried out under the following measuring conditions.

Detector: Ultraviolet absorptiometer (measuring wavelength: 240 nm)

Column: Inertsil ODS 2 4.6×250 mm in which a stainless tube having an inner diameter of 4.6 mm and a length of 25 cm was packed with a 5-μm octadecylsilyl silica gel for liquid chromatography.

Column temp.: Around 40° C.

Mobile phase: 0.1 wt % ammonium acetate:methanol (45:55)

Flow rate: 1 mL/min

When the test liquid was water (FIG. 2), the concentration of dissolution of crystalline compound A produced in Comparative Example 1 in this system was not more than 1 μg/mL. For the powders (amorphous compositions) produced in Examples 2 and 3, the concentration of dissolution was about 18 μg/mL, and this concentration was maintained for 4 hr. For the amorphous compound produced in Example 1, the concentration of dissolution reached about 5 μg/mL and then lowered to about 3 μg/mL. This lowering in concentration is considered attributable to crystallization of the amorphous compound in water. On the other hand, when the test liquid was the 1 wt % aqueous methylcellulose solution (FIG. 3), the concentration of dissolution of crystalline compound A produced in Comparative Example 1 was not more than 1 μg/mL as with the case where the test liquid was water, whereas the concentration of dissolution of the amorphous compound produced in Example 1 was not less than about 18 μg/mL and this concentration was maintained for 4 hr. From these results, it appears that methylcellulose suppresses crystallization of the amorphous compound produced in Example 1 rather than contribution to the solubilization of crystalline compound A.

Test Example 3

Dissoluvability Test (2)

Water was provided as a test liquid, and the dissolution of the capsule preparation produced in Example 14 was examined with an elution tester (model NT-6100 manufactured by TOYAMA SANGYO Co., Ltd., automatic measurement by ultraviolet absorptiometry, detection wavelength: 246 nm). Specifically, the capsule preparation produced in Example 14 (containing 100 mg of amorphous compound A produced in Example 1) was added to 900 mL of water (37° C.), followed by stirring with a paddle at 100 rpm. The results were as shown in FIG. 4.

For the amorphous compound produced in Example 1, the concentration of dissolution in water was rapidly lowered (FIG. 2), while the lowering in concentration of dissolution did not occur in an aqueous methylcellulose solution (FIG. 3). This dissolution was the same as the dissolution of the amorphous compositions produced in Examples 2 and 3. From the above results, it is considered that methylcellulose and/or hydroxypropylmethylcellulose may be formulated as an ingredient in the production of a preparation using the amorphous compound.

As a result of the dissoluvability test, carried out in water, of the capsule preparation produced in Example 14 while taking the above fact into consideration (FIG. 4), it was found that the amorphous compound produced in Example 1 formulated into the capsule preparation did not cause a rapid lowering in concentration of dissolution as shown in FIG. 2. These results show that the amorphous compound produced in Example 1 is also useful as a raw material of a pharmaceutical preparation and that the dissolution of the amorphous compound can be maintained by separately formulating methylcellulose and/or hydroxpropylmethylcellulose as a pharmaceutical additive.

Test Example 4

Absorption Test

Compound A, when absorbed in the living body, is converted to a substance, which develops its physiological activity, that is, 7,8-dimethoxy-4(5H), 10-dioxo-2H-1,2,3-triazolo[4,5-c][1]benzazepine (WO 95/18130; hereinafter referred to as "compound B").

The sample produced in Comparative Example 1 or Example 1 was suspended in a 1 wt % aqueous methylcellulose solution. The suspension was administered orally to beagles (n=6) which had been subjected to fasting overnight. As a result, the compound B concentration of plasma over time was as shown in FIG. 5. The difference in absorption among the samples was evaluated by comparing the area under the plasma drug concentration-time curve (AUC).

The plasma drug concentration in the collected blood was quantitatively determined according roughly to the following method.

Blood (about 0.7 mL) collected from the cephalic vein was centrifuged (4° C., about 9000×g, 10 min) in the presence of heparin to obtain plasma. Methanol (400 μL) and an internal standard substance solution (sodium salt of 7-methyl-4(5H),10-dioxo-2H-1,2,3-triazolo[4,5-c][1]benzazepine, 100 ng/mL, 100 μL) were added to the plasma (100 μL), and the mixture was stirred and centrifuged (4° C., about 9000×g, 10 min).

The supernatant was evaporated to dryness at room temperature under a nitrogen gas stream, and 150 μL of a mixed solution composed of a 10 mmol/L phosphate buffer (pH 7.0) and a methanol (8:2) was added to the residue for redissolution. The solution was then filtered by a centrifugal filter (Centricut Ultra-Mmini (KURABO INDUSTRIES LTD.), 4° C., about 9000×g, 10 min), and the filtrate was analyzed as a sample by HPLC. In this Test Example 4, HPLC was carried out under the following measuring conditions.

HPLC pump: PU-980 (Japan Spectroscopic Co., Ltd.)
Degassor: DG-980-50 (Showa Denko K.K.)
Autosampler: AS-950-10 (Japan Spectroscopic Co., Ltd.)
Detector: FP-920 (Japan Spectroscopic Co., Ltd.)
Fluorescence detection wavelength: Ex 270 nm, Em 466 nm (GAIN=100, response=standard)

Column: CAPCELLPAC C18 UG 120 (4.6×250 mm, 5 µm, Shiseido Co, Ltd.)

Column temp.: 40° C.

Mobile phase: Linear gradient using 10 mmol/L phosphate buffer (pH 7.0) and methanol (8:2→2:8)

Flow rate: 1.0 mL/min

Injection volume: 20 µL

As compared with oral administration of the crystalline compound produced in Comparative Example 1, the plasma compound B concentration after the administration of the amorphous compound produced in Example 1 was significantly higher. Further, even when the amorphous compound produced in Example 1 was administered at a dose which is one-eighth of the dose of the crystalline compound produced in Comparative Example 1, in a change in the plasma compound B concentration over time, the plasma compound B concentration in the case of the administration of the amorphous compound produced in Example 1 was much higher than the plasma compound B concentration in an animal group to which the crystalline compound produced in Comparative Example 1 had been administered. These facts demonstrate that the amorphous compound produced by the present invention had significantly improved absorption. The same results were obtained when cynomolgus monkeys were used.

The invention claimed is:

1. A composition comprising an amorphous compound 2-(1-isopropoxy-carbonyloxy-2-methylpropyl)-7,8-dimethoxy-4(5H), 10-dioxo-2H-1,2,3-triazolo[4,5-c][1]benzazepine having no diffraction peak in a powder X-ray diffraction pattern and a solubility of 15 to 20 µg/mL in a 1 wt % methylcellulose solution at 37° C. and methylcellulose and/or hydroxypropylmethylcellulose.

2. The composition according to claim 1, wherein the mixing ratio of the amorphous compound of 2-(1-isopropoxy-carbonyloxy-2-methylpropyl )-7,8-dimethoxy-4(5H), 10-dioxo-2H-1,2,3-triazolo[4,5-c][1]benzazepine to the total amount of methylcellulose and/or hydroxypropylmethylcellulose is in the range of 1:0.01 to 2.

3. A composition comprising 2-(1-isopropoxy-carbonyloxy-2-methylpropyl)-7,8-dimethoxy-4(5H), 10-dioxo-2H-1,2,3-triazolo[4,5-c][1]benzazepine having no diffraction peak in a powder X-ray diffraction pattern and a solubility of 15 to 20 µg/mL in a 1 wt % methylcellulose solution at 37° C. and a polymer compound, wherein the polymer compound is one or at least two compounds selected from the group consisting of ethylcellulose, hydroxypropylmethylcellulose phthalate, hydroxypropylcellulose, carboxymethylethylcellulose, polyvinyl pyrrolidone, polyvinyl acetal diethylaminoacetate, methacrylic acid copolymer L, aminoalkyl methacryl acrylate copolymer E, and vinyl acetate-vinylpyrrolidone copolymer.

4. A process for producing the composition according to claim 1, said process comprising the steps of: dissolving 2-(1-isopropoxycarbonyloxy -2-methylpropyl )-7,8-dimethoxy-4(5H), 10-dioxo-2H-1,2,3-triazolo [4,5-c][1]benzazepine and methylcellulose and/or hydroxypropylmethylcellulose in methylene chloride to prepare a solution; and then spray-drying the solution.

5. A process for producing the composition according to claim 3, said process comprising the steps of: dissolving 2-(1-isopropoxycarbonyloxy-2-methylpropyl)-7,8-dimethoxy-4(5H), 10-dioxo-2H-1,2,3-triazolo[4,5-c][1]benzazepine and the polymer compound in methylene chloride or a methylene chloride/lower alcohol mixed solvent to prepare a solution; and then spray-drying the solution.

6. The process according to claim 5, wherein the lower alcohol is an alkyl alcohol having 1 to 3 carbon atoms.

7. A pharmaceutical composition for oral administration, comprising the composition according to claim 1 and a pharmaceutically acceptable carrier.

8. A pharmaceutical composition for oral administration, comprising the composition according to claim 2 and a pharmaceutically acceptable carrier.

9. A pharmaceutical composition for oral administration, comprising the composition according to claim 3 and a pharmaceutically acceptable carrier.

10. A method for treating an allergic disease, wherein said method comprises the step of administering the composition according to claim 1 to an animal.

11. A method for treating an allergic disease, wherein said method comprises the step of administering the composition according to claim 2 to an animal.

12. A method for treating an allergic disease, wherein said method comprises the step of administering the composition according to claim 3 to an animal.

13. The method of any one of claims 10-12 wherein said animal is a human.

* * * * *